United States Patent [19]

Gawol et al.

[11] Patent Number: 4,762,523

[45] Date of Patent: Aug. 9, 1988

[54] PERMANENTLY NON-DUSTING PIGMENT AND DYE PREPARATIONS, METHOD FOR PRODUCING THEM, AND MEASURING DEVICE THEREFORE

[75] Inventors: Manfred Gawol, Clausthal-Zellerfeld; Gerhard Adrian, Goslar, both of Fed. Rep. of Germany

[73] Assignee: Dr. Hans Heubach Gmbh & Co. KG, Langelsheim, Fed. Rep. of Germany

[21] Appl. No.: 763,437

[22] PCT Filed: Nov. 30, 1984

[86] PCT No.: PCT/EP84/00380

§ 371 Date: Aug. 1, 1985

§ 102(e) Date: Aug. 1, 1985

[87] PCT Pub. No.: WO85/02407

PCT Pub. Date: Jun. 6, 1985

[30] Foreign Application Priority Data

Dec. 2, 1983 [DE] Fed. Rep. of Germany ....... 3343743
Dec. 2, 1983 [DE] Fed. Rep. of Germany ....... 3343742
Dec. 8, 1983 [DE] Fed. Rep. of Germany ....... 3344464
Dec. 8, 1983 [DE] Fed. Rep. of Germany ....... 3344463

[51] Int. Cl.$^4$ .................. C09B 67/42; C09C 3/08; C09K 3/22

[52] U.S. Cl. ........................... 8/524; 8/526; 8/552; 8/580

[58] Field of Search ...................... 8/524, 526

[56] References Cited

U.S. PATENT DOCUMENTS

| | | | |
|---|---|---|---|
| 3,499,315 | 3/1970 | Marino | 73/38 |
| 3,560,134 | 2/1971 | Streck | 8/617 |
| 3,778,287 | 12/1973 | Stansfield et al. | 106/308 Q |
| 4,069,013 | 1/1978 | Hett et al. | 8/609 |
| 4,117,717 | 10/1978 | Isley | 73/38 |
| 4,295,851 | 10/1981 | Neumann et al. | 8/527 |
| 4,402,702 | 9/1983 | Kaspar et al. | 8/586 |
| 4,425,134 | 1/1984 | Bruttel et al. | 8/524 |

FOREIGN PATENT DOCUMENTS

| | | |
|---|---|---|
| 190255 | 10/1981 | Czechoslovakia . |
| 23638 | 2/1981 | European Pat. Off. . |
| 576100 | 3/1946 | United Kingdom . |
| 1442538 | 7/1976 | United Kingdom . |

*Primary Examiner*—A. Lionel Clingman
*Attorney, Agent, or Firm*—Browdy and Neimark

[57] ABSTRACT

Permanently non-dusting pigment and dye preparations, which contain as dedusting agents,
(a) a surface-active substance in an amount of from 0.5 to 10%, and
(b) a substance which after mixing of the dried mixture of pigment and surface-active substance causes the mixture, upon repeated intensive shear stress, to reach the smear point, contained in an amount (depending on the fineness, morphology and later intended use of the pigment and dye preparations) of from 2 to 25%, the remainder comprising the pigment or dye, wherein the preparations can be obtained by adding to the filter suspension of the pigment or dye a surface-active substance, or mixtures thereof, which is or are suitable in accordance with the type of pigments or dyes and with the particular intended use, and after homogeneous distribution the combination of pigment and surface-active substance, optionally after isolation in the form of a press cake, is dried, and the dried product is subsequently added to an agent which is liquid and flowable or becomes liquid at an elevated temperature, which upon intensive shear stress causes the mixture to reach the smear point, mixing is performed applying an intensive shear stress, until the smear point is reached, and then granulation is subsequently performed, in a manner known per se, if needed; and a dust measuring device in which the conditions leading to dust production are maintained during the entire measuring operation.

8 Claims, No Drawings

PERMANENTLY NON-DUSTING PIGMENT AND DYE PREPARATIONS, METHOD FOR PRODUCING THEM, AND MEASURING DEVICE THEREFORE

DESCRIPTION

In the field of pigments and dyes, there are increasing attempts being made to produce dust-free and non-dusting preparations, which do not emit dust while being processed. Such non-dusting preparations are particularly desirable so as to avoid color contamination when various products are handled, and they also make accurate apportioning possible. Dust losses are avoided, and because it is cleaner and safer to work with such preparations, the health risk involved in working with toxic pigments and dyes is also reduced.

The safest procedure is to use paste preparations, adding enough of such additives as surface-active substances and solvents as to attain a non-dusting, pasty state. The agents required for a particular application, such as dispersing agents, anti-settling agents and binders, are often also incorporated at the same time. In such pastes, the pigment concentration depends on the fineness and texture of the given pigment as well as on the amount of binder it requires and may be between approximately 30 and 90%. In producing the pigment pastes, the starting material is dried pigment, which is mixed with the various components.

The disadvantage of the pigment pastes is that they are difficult to apportion, and they necessitate careful cleaning of the packing drum.

The object of the present invention is to produce non-dusting pigment and dye preparations which are nevertheless flowable and thereby enable simple apportioning and weighing and which maintain this state permanently.

Quite a number of methods are already known. According to German patent application DE-OS No. 27 23 921, the tendency of metal chromates to produce dust is suppressed by adding a combination of phthalic and terephthalic acid esters and esters of fatty acids, along with surface-active substances, to an aqueous suspension of pigment and drying it after filtration. Such preparations produce less dust, but they are not premanently non-dusting. A product produced according to Example 1 of the above patent application yielded a dust production value of 83 mg/100 g, as measured with the Heubach dust-production measuring device. Further methods and agents are disclosed in German patent applications DE-OS No. 29 31 771 and DE-OS No. 25 23 096, U.S. Pat. No. 3,560,134, European patent application EU-OS No. 0056 160 and German patent application DE-OS No. 28 41 566.

The subject of the present invention is permanently non-dusting pigment and dye preparations, which in addition to from 75 to 97.5% pigment contain a surface-active substance in an amount from 0.5 to 10% and from 2 to 25% of an agent which was the pigment when intensive shear stress is applied (i.e., causes the dried, homogeneous mixture of pigment or dye and surface-active substance to reach the wet point, also referred to herein as the smear point). Any surface-acitve agent suitable for the particular pigment or dye type used and for the intended later application can be used as the surface-active substance; examples include ionic or non-ionic agents available on the market. However, a long-chain polyester of the "highly effective dispersing agent" type is particularly preferred, in particular a polyester produced by homopolymerization of a saturated or unsaturated aliphatic $\omega$-hydroxycarboxylic acid with at least 4 carbon atoms between the hydroxy group and the carboxy group and a total of at least 9 carbon atoms including the carboxy group, or by polymerizing a mixture of a hydroxycarboxylic acid of this kind and a carboxylic acid lacking hydroxy groups, in particular one having up to 20 carbon atoms.

Among these suitable polyesters are those described in German patent application DE-OS No. 21 62 484, which are hereby expressly incorporated by reference.

What is essential here is that the surface-active substance is not applied to the dry pigment, nor has the pigment already been dried; instead, the still-moist pigment, as it comes from the production process, is treated with the surface-active substance, because otherwise the desired surface properties are not obtained. Therefore the agent is suitably also mixed with the pigment suspension and only then is it dried. The term "pigment" also includes dyes.

Any substance that, after being introduced into the dry mixture of pigment and surface-active substance that is to be attained, wets the pigment under intensive shear stress can be used, and the various technical requirements of the fields of application, such as enamels, paints, printing inks and plastic dyes, can be taken into consideration at the same time. Among these are water, organic solvents, plasticizers and substances which become liquid in response to elevated temperatures, such as waxes. As used hereinafter, the term "liquid" refers to a substance which is liquid at least under the conditions under which intensive sheet stress is latter applied, and which is capable of wetting the surfactant-modified pigment. Useful agents here are those which either do not volatilize, or do not do so significantly. For reasons of economy, mineral oil is generally preferred, because it brings about excellent results and is relatively inexpensive.

As the mineral oil, aliphatic, alicyclic and/or aromatic hydrocarbons which are flowable at room temperature and the boiling point of which is above 70° C. are particularly useful. Aliphatic hydrocarbons which may contain various quantities of cycloaliphatic and/or aromatic hydrocarbons are preferred. This category thus includes not only technical grade mineral oils made from variously refined crude oils but also synthetic hydrocarbons, such as Fischer-Tropsch mixtures with the given boiling ranges. Accordingly, this includes all unsaponifiable substances of arbitrary origin, mainly comprising hydrocarbons, obtained for example from crude oil, froms tars or the distillation products thereof, or from low-temperature carbonization.

Special preference is given to synthetic isoparaffins. However, water is also very suitable, and in particular from 10 to 15% of water can be added when small quantities of surface-active agent are employed. In the case of preparations made non-dusting by the addition of water, the end product should then be packaged in watertight or vapor-tight containers, so that no significant amounts of water can escape.

These permanently non-dusting pigment preparations are produced by adding 0.5 to 10% by weight, relative to the total weight of the end product, of a suitable surface-active agent to the filter suspension of the pigment; after homogeneous distribution, the combination of pigment and surface-active agent, which may optionally have been isolated in the form of a press cake, is dried, and the dried product is then mixed with an carrier which brings the mixture to the smear point when intensive shear stresses are applied, this carrier being in particular mineral oil having a boiling range from 70° to 360° C., preferably 180° to 280° C., and especially 180° to 250° C.; intensive shear stress is applied unitl the smear point is reached, and then the product is granulated in a manner known per se if desired.

If water is to be used as the substance that brings the mixture to the smear point, this water can be added subsequently, or else the mixture of pigment or dye and surface-active agent, the latter perhaps in the form of a press cake, is not fully dried, so that a residual water content of 2 to 25%, and in particular 10 to 15%, remains, and the moist mixture thus obtained is brought to the smear point by the application of shear stress and, if desired, granulated. This water content is then present in the end product as well, aside from slight changes occurring during further processing.

The homogeneous distribution of the surfactant in the filter suspension of the pigment is achieved by performing thorough mixing in a known manner. Isolation as a press cake is achieved by means of suitable filtration devices, such as filter presses, drum filters, suction filters, etc., which yield a press cake or an equivalent adequately water-free product which can then be dried in a technically apropriate manner.

Treatment with the substance which brings the mixture to the smear point is carried out in such mixing apparatus as a kneader mixer, intensive mixer, paddle mixer or any other suitable device which generates sufficient shear stress and brings the product to the smear point within no longer than approximately 2 hours. Preference is given to degrees of shear stress by which the smear point is attained within 15 to 45 minutes, and in particular within about half an hour. In the process, the product usually appears in the form of a flowable fine granulate which is practically non-dusting.

Within the meaning employed in this patent application, the smear point is reached before a cohesive, putty-like mass, as defined for example by determining the oil adsorption according to DIN 53199 (see also Ullmanns Encyklopaedie der technischen Chemie [Ullman's Encyclopedia of Industrial Chemistry], 4th edition, Volume 18, page 565), has formed. The smear point as defined in this patent application is reached just when the pigments are wetted by the liquid agent. This wetting is most easily determined by observing the point at which the liquid agent/pigment mixture produces a slight smearing effect on the walls of the mixing devices. Hence the amount of dust-binding agent, such as oil, required to achieve this smear point is less than the amount of oil required to determine the oil adsorption according to DIN No. 53199.

By adding the surface-active substance to the pigment suspension before drying is carried out, optimum wetting is achieved, which makes it possible to obtain a virtually absolutely non-dusting pigment preparation by adding mineral oil, for example, to the dried product comprising pigment and surface-active substance. Only relatively small quantities of mineral oil are needed. When equal amounts of surface-active substance and mineral oil are added to the previously dried product, almost twice as much mineral oil is needed, e.g., more than 20%, instead of 10% as in the method according to the present invention, to achieve the same degree of absence of dust production.

This method can be applied in principle to all pigments and dyes which are in the wet state and are separated out as a filter suspension. It can be used equally well for inorganic and organic pigments and dyes such as lead chromate, lead molybdate, zinc chromate, mixed-phase pigments such as nickel-titanium yellow, chrome-titanium yellow, etc., phthalocyanines, anthraquinones, azo pigments, lake-type azo pigments, disazo condensation pigments, isoindolines, indigoid dyes, quinachridones, and perylenes, among others.

The mixture of pigment or dye suspension, which usually contains about 50% water, and surface-active agent is first thoroughly homogenized and then either dried directly or, if it is desired that the water content be reduced further, it is further dewatered in a suitable press, for instance a high-pressure press, and only then taken to the drying stage, thereby saving drying costs. In this way it is possible to obtain press cakes having a solids content of up to 85%. This mixture can be dried in the usual manner, for instance on belt or suspended-belt dryers with an ambient temperature of 120° to 130° C., or in vacuum dryers where temperatures of 100° to 120° C. are normally used. Since the mixture contains organic material, care should be taken to insure that the drying conditions, in particular the temperature, do not cause any damage to the material, for instance by local overheating.

The dust-producing characteristics are determined in a Heubach dust production measuring device, which is illustrated in the appended drawing figure.

This dust production measuring device was developed in order to be able to perform extremely accurate analyses of the dust-producing tendencies of powdered and granular substance, because quantitative information about dust-producing behavior is important for the sake of safe industrial processes and operations. The tendency toward dust production was heretofore judged by analogy with the proportion of fines in the starting material, or by estimation, but such methods can give rise to considerable errors, because dust particles are frequently generated only by some type of movement and by abrasion; in constrast, the tendency to produce dust during materials handling is ascertained herein in a manner that very closely approximates actual conditions. To this end, the test material remains in motion during the entire period of measurement. This is achieved by keeping powder or granular materials in motion in a dust-generating vessel 2, having a 2.5 liter capacity, for 5 minutes at 30 rpm. Built-in baffles simulate events during conveyance, and the dust particles are picked up by an air flow which carries them out of the dust-generating vessel and deposits them on a filter 4 having a defined porosity. Coarser particles are retained in a coarse separator 3. The air is drawn through the system by a vacuum pump 5, and it is then recorded by an air lock equipped with an air flow meter 6 and discharged. A motor 1 drives the system.

Compared with a dust production measuring device, in which the dust value is measured by the attenuation of a beam of light passing through a collecting container, the attenuation being caused by the swirling up of dust produced when the test sample is dropped once into the container, the device according to the invention has the advantage that it measures a state that very closely approximates that encountered in actual practice, such as during conveying, mixing and filling operations.

| Test Data: | |
|---|---|
| Sample weight | 100 g |
| Measuring time | 5 min |
| Speed | 30 rpm |
| Air flow | 0.25 liters/sec |
| Dust-generating vessel | 2.5 liter capacity |

The following examples will explain the invention. A non-dusting preparation is assumed to be one which yields dust production values of 0 to a maximum of 5 mg/100 g when measured with the Heubach dust production measuring device.

EXAMPLE 1

1 kg of chromate pigment suspension was combined with 15 g of the polyester-based surface-active substance and well mixed with the aid of a stirrer. Following drying, the pigment was mixed with 10% of mineral oil in a kneader or paddle mixer and the intensive mixing was continued until such time as a uniform distribution of the additives was achieved. This state is recognized from the fact that a flowable, non-dusting fine granulate is formed. Usually this takes about 30 minutes. The treated finished product was measured using the Heubach dust production measuring device, and a dust production value of 0 mg/100 mg of pigment was obtained. The non-treated, dried pigment sample yielded a dust production value of 90 mg/100 g.

EXAMPLE 2

10 g of polyester-based surface-active substance was added to 1 kg of 50% zinc chromate suspension and mixed by stirring well. Following drying, the pigment was mixed with 13% of mineral oil in a kneader or paddle mixer and then subjected to the shear effects of the mixing device until the mineral oil was fully homogeneously distributed. After about 30 minutes, a non-dusting, flowable fine granulate was obtained having a dust production value of 0, as measured by the Heubach dust production measuring device. The untreated, dried sample of zinc chromate pigment yielded a dust production value of 250 mg/100 g.

EXAMPLE 3

300 g of phthalocyanine press cake (approximately 36% solids) was combined with a mixture of 150 g isopropanol, 5.5 g aminomethyl propanol and 8.2 g of the polyester-based surface-active substabce; then, after the addition of 100 g of water, it was stirred for about 30 minutes with a dissolver. The pigment suspension prepared in this way was dried in a drying cabinet and after intermediate grinding in a laboratory mill it was mixed in a mixer with 20% of mineral oil (relative to the solids content) and the intensive mixing was continued until homogeneous distribution of the additives was achieved. After 20 to 30 minutes, a non-dusting, flowable fine granulate had formed, the dust production value of which was 5 mg/100 g when measured with the Heubach dust production measuring device. Non-prepared phthalocyanine pigments have dust production values of 2500 to 3500 mg/100 g.

EXAMPLE 4

A mixture of 23 g of aminomethyl propanol and 25 g of the polyester-based surface-active substance was added to 1568 g of an anthraquinone pigment suspension (solids content approximately 28%) and stirred for about 30 minutes in a dissolver. In order to prevent foaming, 7.5 g of a defoaming agent were also added. The suspension prepared in this way was dried in a drying cabinet and then pre-ground in a laboratory mill.

The preparation was placed in a mixer and combined with 20% of mineral oil, and then mixing was continued for about 30 minutes. This yielded a flowable, non-dusting fine granulate with a dust production value of less than 5 mg/100 g of pigment as measured with a Heubach dust production measuring device. Dried, unprepared anthraquinone pigments have extraordinarily high dust production values of 3500 to 4500 mg/100 g.

EXAMPLE 5

1 kg of 50% chromate pigment suspension was combined with 15 g of the polyester-based surface-active substance and well mixed with the aid of a stirrer. Following drying, the pigment was combined with 15% of molten wax in a heatable kneader mixer and intensive mixing was performed until uniform distribution of the additive had been achieved. This state is recognized from the fact that a flowable non-dusting granulate is formed. Generally, this takes about 30 minutes to occur. The pigment was first brought to a temperature that was above the melting point of the wax. A wax with a melting point of 79° C. was used.

The dust production measured for the preparation produced in this way was 5 mg/100 g. The measurement was performed with a Heubach dust production measuring device.

Naturally the auxiliary agents, such as dispersing or anti-abrasion agents, which are required for specific applications can be added directly to the preparation according to the invention. Such agents are suitably added together with the addition of the agent (b) which brings the mixture to the smear point. Similarly, as demonstrated in one of the examples, auxiliary agents for the mixing or kneading process, such as anti-foaming agents, can be added during the appropriate stage. All these auxiliary agents are used in the technically customary and well-known quantities, which can be determined by performing a few preliminary experiments for a particular case, i.e., as a function of the quantity and type of the surface-active agent and the quantity and type of the agent that brings the mixture to the smear point.

The following preferred embodiments of the invention are named:

As additive b, an additive which is liquid, or becomes liquid above 50° C., is present in the preparations. As the liquid additive, water, in particular, or a mineral oil with a boiling range up to 360° C., preferably 180°–280° C., can be present, while the additive that is liquid at the higher temperature preferably has a melting point of from 50° to 200° C. The substance leading to the smear point is added in a quantity of from 2 to 25% by weight, in terms of the end product, or (if evaporation takes place) in a quantity such that a content of 2 to 25% by weight is attained in the end product. In the case of mineral oil, the additive preferably amounts to 5 to 15%, in particular 10%. The additive that becomes liquid above 50° C. can in particular be a wax or paraffin substance. The filter suspension of the pigment or dye that is homogenized with the surface-active substance is isolated in the form of a press cake by means of suitable filter systems, such as a filter press, suction press, drum filter and the like.

It is essential that what is treated with the surface-active agent is the still-moist pigment, dewatered only mechanically, for instance being pressed out or centrifuged, but even if a slight drying effect occurs, for instance by air or warm air drying, still generally moist. That is, the surfaces of the pigment particles are not dried but are instead still moist, even if the dampness on these surfaces is reduced as compared with the moistness within the filter suspension press cake. The term "pigment" here encompasses dyes as well.

What is claimed is:

1. Permanently non-dusting pigment preparations produced by a process comprising the steps of:
   thoroughly mixing a long-chain polyester surfactant produced by condensation of at least one saturated or unsaturated aliphatic $\omega$-hydroxycarboxylic acid with at least 4 carbons between the hydroxy group and the carboxy group and a total of at least 9 carbon atoms including the carboxy group or by condensing said at least one hydroxycarboxylic acid with a carboxylic acid lacking hydroxy substitution, in an amount of from 0.5 to 10%, with a moist press cake of said pigment;
   drying said surfactant-containing mixture;
   adding an essentially non-volatile liquid selected from the group consisting of mineral oil and molten wax to said dried mixture, in an amount of 2-25%, based on said dried mixture;
   applying intensive shear stress to said liquid-containing mixture until said pigment is wetted by said liquid, thereby obtaining a flowable, non-dusting granulate.

2. The product of claim 1, wherein said surfactant-containing mixture was formed into a press-cake prior to drying.

3. A process for preparing a permanently non-dusting pigment, comprising the steps of:
   mixing a long-chain polyester surfactant produced by condensation of at least one saturated or unsaturated aliphatic $\omega$-hydroxycarboxylic acid with at least 4 carbons between the hydroxy group and the carboxy group and a total of at least 9 carbon atoms including the carboxy group or by condensing said at least one hydroxycarboxylic acid with a carboxylic acid lacking hydroxy substitution, in an amount of from 0.5 to 10%, with a moist press cake of said pigment;
   drying said surfactant-containing mixture;
   adding an essentially non-volatile liquid selected from the group consisting of mineral oil and molten wax to said dried mixture;
   applying intensive shear stress to said liquid-containing mixture until said pigment is wetted by said liquid, thereby obtaining a flowable non-dusting granulate.

4. A method as defined by claim 3, wherein the surfactant is used in an amount of from 0.5 to 10%.

5. A method as defined by claim 3, wherein the liquid has a melting or liquification point of from 50° to 200° C. and is used in an amount of from 5 to 25%.

6. A method as defined by claim 3 wherein the surfactant is used in an amount of from 1 to 5%.

7. A method as defined by claim 4, wherein the carrier a melting point or liquification of from 50° to 200° C., and is used in an amount of from 5 to 25%.

8. A method as defined by claim 7, wherein the intensive shear stress is applied in an intensive mixer, kneader, or paddle mixer.

* * * * *